United States Patent [19]

Kaasenbrood et al.

[11] 4,036,878

[45] July 19, 1977

[54] PROCESS FOR PREPARING UREA

[75] Inventors: Petrus J.C. Kaasenbrood, Sittard; Petrus J.M. Van Nassau, Munstergeleen, both of Netherlands

[73] Assignee: Unie Van Kunstmestfabrieken, B.V., Utrecht, Netherlands

[21] Appl. No.: 622,417

[22] Filed: Oct. 14, 1975

Related U.S. Application Data

[63] Continuation of Ser. No. 369,388, June 12, 1973, abandoned.

[30] Foreign Application Priority Data

June 12, 1972 Netherlands .................. 7207941

[51] Int. Cl.$^2$ .......................................... C07C 126/00
[52] U.S. Cl. ............................................. 260/555 A
[58] Field of Search ................................ 260/555 A

[56] References Cited

U.S. PATENT DOCUMENTS

| | | | |
|---|---|---|---|
| 2,848,493 | 8/1958 | Dewling et al. | 260/555 A |
| 3,317,601 | 5/1967 | Otsuka et al. | 260/555 A |
| 3,356,723 | 12/1967 | Kaasenbrood | 260/555 A |
| 3,378,585 | 4/1968 | Fauser | 260/555 A |
| 3,514,484 | 5/1970 | Wentworth | 260/555 A |
| 3,725,210 | 4/1973 | Otsuka et al. | 260/555 A |
| 3,759,992 | 9/1973 | Maurovic | 260/555 A |
| 3,876,696 | 4/1975 | Guadalupi et al. | 260/555 A |
| 3,929,878 | 12/1975 | Maurovic | 260/555 A |
| 3,936,500 | 2/1976 | Kaasenbrood et al. | 260/555 A |

*Primary Examiner*—O. R. Vertiz
*Assistant Examiner*—Eugene T. Wheelock
*Attorney, Agent, or Firm*—Cushman, Darby & Cushman

[57] ABSTRACT

Unreacted free ammonia and ammonium carbamate are removed from a urea synthesis solution efficiently by first heating the solution up to 205°–250° C and then, in a second, separate step, stripping the heated solution with a stripping gas but under adiabatic conditions to remove the unreacted materials. The process is applied as an integral part of a continuous urea preparation.

6 Claims, 1 Drawing Figure

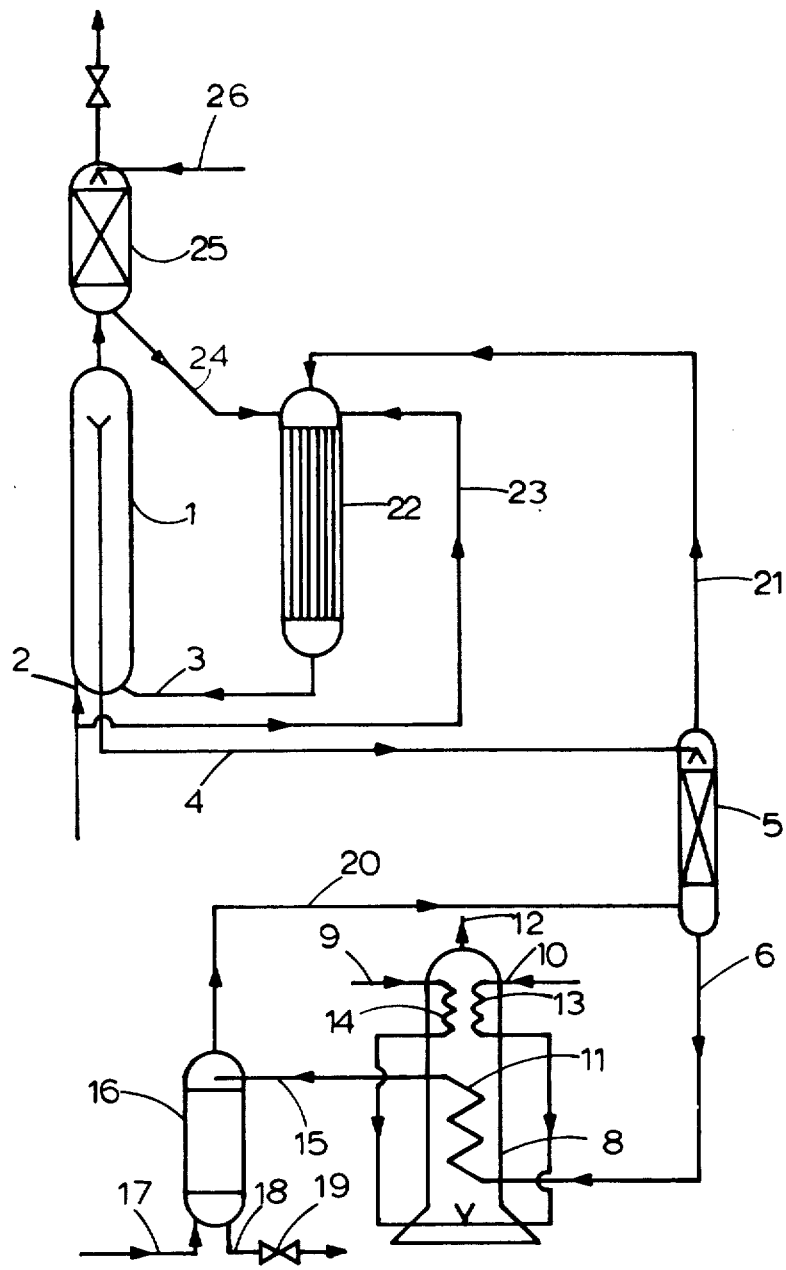

PROCESS FOR PREPARING UREA

This is a continuation of application Ser. No. 369,388, filed June 12, 1973, now abandoned.

BACKGROUND OF THE INVENTION

The preparation of urea from ammonia and carbon dioxide occurs in two steps, via the intermediate product ammonium carbamate and under the usual conditions of temperature and pressure, the conversion of ammonia and carbon dioxide into ammonium carbamate according to the exothermic reaction:

$$2NH_3 + CO_2 \rightleftarrows NH_2COONH_4 + a \text{ kcal}$$

is practically complete, while the conversion of the ammonium carbamate ($NH_2COONH_4$) into urea according to the endothermic reaction:

$$NH_2COONH_4 \rightleftarrows CO(NH_2)_2 + H_2O - b \text{ kcal}$$

is only a partial one.

In practice the urea synthesis is carried out in the presence of an excess quantity of ammonia in order to increase the conversion to urea to a higher degree. The solution obtained during the synthesis therefore contains, in addition to urea and water, unconverted ammonium carbamate and free ammonia, and these materials should be removed from the solution before it can be concentrated and processed into an acceptable end-product.

According to a known process as described in Dutch Patent Specification No. 101,446 and U.S. Pat. No. 3,356,723 this is done by subjecting the urea synthesis solution that remains after urea synthesis under pressure to a stripping treatment with gaseous carbon dioxide, in which the ammonium carbamate is decomposed into ammonia and carbon dioxide, with the expulsion of a gas mixture consisting of ammonia, carbon dioxide and water vapor. The decomposition of the ammonium carbamate and the expulsion of the ammonia and carbon dioxide are carried out in the stripping process by reducing the partial pressure of one of the two reactants with the aid of the stripping gas and by the addition of heat. In order to accomplish this the urea synthesis solution is made to flow in a downward direction as a thin film along the internal walls of a number of heated vertical tubes and in a countercurrent with the stripping gas. In this known process therefore the amount of heat necessary for the decomposition of the ammonium carbamate is supplied during the expulsion from the urea synthesis solution of part of the reactants liberated by the decomposition, the expulsion being carried out with the aid of the stripping gas. Stripping is effected counter-currently in order to achieve as favorable an expulsion efficiency of the ammonia and carbon dioxide as possible which are the unconverted reactants. The disclosure of U.S. Pat. No. 3,356,723 is incorporated herein by reference to the extent necessary to understand the process as described herein, it being understood that the present invention represents an improvement over the process described in said U.S. patent.

In this known process however there is a risk of undesirable flooding phenomena occurring for, in the case of flooding, the liquid film flowing downward in the tubes is, as it were, peeled from the wall by the ascending gas and as a result the film becomes detached from the wall which may cause the formation of liquid plugs which occlude the affected tubes. Flooding phenomena usually occur in the presence of high gas and liquid loads and, hence, occur first in the top part of the tubes because here these loads are highest. They result from the application of the counter-current principle and their occurrence is further promoted by the addition of heat via the tube wall simultaneously with the stripping, since this causes the liberated heat to flow in a direction away from the wall. In this connection, in order to avoid flooding, only a limited heat flux can be allowed for a given tube diameter and at given gas and liquid loads, hence placing practical limitations on the process. The present invention provides a method of eliminating this by adding sufficient heat to the urea synthesis solution to cause decomposition of a major portion of the ammonium carbamate prior to contact with the stripping gas.

DETAILED DESCRIPTION OF THE INVENTION

The present invention therefore relates to a process for preparing urea, in which as is known processes ammonia and carbon dioxide are reacted at a pressure of 80 to 200 atm and a temperature of 170° to 190° C, the resulting urea synthesis solution formed from the reaction is heated and counter-currently contacted with a stripping gas. The gas mixture which then forms consists mainly of ammonia, carbon dioxide and water vapor and is recirculated to the urea synthesis area. The process according to the present invention is characterized in that the urea synthesis solution is heated prior to stripping in a heat exchange zone to a temperature of 205° to 250° C, and that subsequently in a stripping zone the reactants present which have not been converted into urea are expelled with the aid of the stripping gas under adiabatic conditions; in other words no heat is added to the urea synthesis solution in the stripping zone.

The process of the present invention provides for separate stripping and heating steps of the urea synthesis solution, so it is possible for the heating to be carried out co-currently, that is in such a way that the urea synthesis solution and the gases expelled therefrom during the heating both flow through the heat exchange zone in the same direction. No liquid film need then be formed and maintained, nor do flooding phenomena as described above play a part in the improved process, so that higher velocities may be applied. This results in a better heat exchange, so that an appreciably smaller heat-exchange surface area may be applied. The process of the present invention is maximized to full advantage if the heating is carried out in a one-pass heater in which the combustion gases of a gaseous or liquid hydrocarbon fuel are used as heating medium. The residence time of the urea synthesis solution in the heat exchange zone is preferably not longer than 10 seconds in order to keep the hydrolysis of the urea formed within acceptable limits.

The invention will now be further illustrated based on the diagram contained in the attached FIGURE.

In synthesis autoclave 1, at a pressure of 80–200 atm and a temperature of 170°–190° C, a urea synthesis solution is formed from ammonia supplied, via line 2, and a mixture of gas and liquid supplied via line 3, which mixture contains ammonium carbamate, ammonia, dioxide and water. This urea-containing solution is led to one-pass heater 8 via lines 4 and 6, passing through rectifying column 5 for the reason that will be explained in detail below. One-pass heater 8, which is shown schematically, consists mainly of a furnace section, in which with the aid of air supplied via line 9, natural gas supplied via line 10 is combusted, and a heat-exchange section, in which heat from the combustion gases rising out of the furnace section is transferred to the urea synthesis solution flowing through the heat exchange tubes 11 which when supplied has a temperature of 160°–190° C. The temperature of the combustion gases in the heat exchange zone may be regulated by circulation of part of the spent gases. The gas liberated during the heating of the solution flows through the heat exchange tubes in the same direction as the solution and, ultimately, a mixture of gas and liquid having a temperature of 205°–250° C leaves the heater 8. The difference in temperature between the solution and the combustion gases is large and also the heat transfer coefficient is high because of the turbulent two-phase flow occurring in the tubes, so that intensive exchange of heat takes place. As a consequence of this, it is possible that high through-pass rates and a smaller heat-exchange surface area are applied and that the residence time is kept short, which is favorable and desirable in view of the hydrolysis of urea.

The combustion gases which have passed heating tubes 11 leave heater 8 via stack 12, possibly after having transferred a further part of their heat via heat exchange coils 13 and 14 to the natural gas or the combustion air. Of course, it is also possible for this heat to be utilized for heating process streams. The mixture of gas and liquid leaving the tubes 11 is introduced into the top part of column 16 via line 15, in which it is counter-currently contacted with carbon dioxide required for the urea synthesis or another gas and fed into the bottom part of the column via line 17. In column 16 no heat is supplied and the column operates under adiabatic conditions. In this column the liquid is passed as a thin film over or along a number of contacting parts, preferably along the walls 7 of the column as well as a plurality of vertically arranged plates, in order to obtain as large a contact surface as possible.

In column 16 the risk of flooding is negligible because a considerable part of the ammonium carbamate originally present in the urea synthesis solution has already been decomposed into gaseous ammonia and carbon dioxide in heater 8, which are separated off in the top part of column 16. As a result of this the quantity of gas liberated in the rectifying section of column 16 is smaller. Moreover, as follows from the above, the operation of column 16 under adiabatic conditions, which means without supply of heat via a heat-exchange surface, has a favorable influence.

The solution left behind in column 16 after the stripping treatment is led, via line 18 and reducing valve 19, in which the pressure is reduced to 3 to 4 atm, to a low-pressure stage of the process not shown in the figure, hereinafter termed as the low pressure stage, where the small amount of ammonium carbamate still present is decomposed in the usual manner by heating, and the liberated ammonia and carbon dioxide are separated off and condensed with formation of an ammonium carbamate solution, and the aqueous urea solution obtained is concentrated all according to known producedures.

The gas mixture separated off in column 16 contains, in addition to ammonia and carbon dioxide, a considerable amount of water. In order for the water quantity, which is recirculated to the synthesis autoclave together with the recovered ammonia and carbon dioxide, to be reduced in volume to the extent possible, which is necessary to achieve maximum conversion, the gas mixture is counter-currently contacted in rectifying column 5 with the urea solution discharged out of synthesis autoclave 1. In this way an important part of the water passes to the urea synthesis solution which is led to heater 8, while part of the non-converted ammonia and carbon dioxide present in the solution passes to the gas mixture leaving column 5 via line 21. This gas mixture is sent to condenser 22, as are the ammonia supplied via line 23 and the ammonium carbamate solution supplied via line 24 from scrubber 25, in which, with the aid of ammonium carbamate solution recirculated from the low-pressure stage via line 26, ammonia and carbon dioxide are removed from the gas mixture containing inert components which is discharged from synthesis autoclave 1. In condenser 22 the major portion of the ammonia and carbon dioxide supplied is condensed to form ammonium carbamate. The resulting mixture of gas and liquid is led into the bottom part of synthesis autoclave 1 via line 3. Here, the condensation of ammonia and carbon dioxide is completed. The heat liberated thereby is used to meet the heat demands of the endothermic conversion of ammonium carbamate into urea. The heat liberated in condenser 22 may be utilized for production of steam and/or for heating process streams. There are, of course, several different arrangements that may be used. For example, it is not necessary to use a heater in which the heat required for heating the urea synthesis solution is obtained by combustion of natural gas or petroleum. For instance, for heating the urea synthesis solution it is also possible to utilize high-pressure steam which, if necessary, may have been produced in a separate steam raiser. The hot steam condensate then formed may be returned to the steam raiser direct, so that a simple, closed circuit is obtained.

The invention will be further illustrated by the following example with reference to the drawing and the arrangement thereof.

EXAMPLE

For preparation of 1,000 tons of urea a day, 567 tons of $NH_3$ and 734 tons of $CO_2$ are needed. Using the process of the present invention and the embodiment described on the basis of the figure, 259 tons of $NH_3$ are supplied via line 2 to synthesis autoclave 1 and the remaining 308 tons via line 23 to condenser 22. Synthesis autoclave 1 is further supplied via line 3 with a mixture of gas and liquid whose gross composition is as follows:
 1,350 tons of $NH_3$
 1,433 tons of $CO_2$
 177 tons of $H_2O$.

The pressure at which the urea synthesis, the rectification, the heating and the stripping of the synthesis solution and the condensation of the gas mixture expelled during the stripping and the rectification take place amounts to 140 kg/cm². The urea synthesis solution supplied to the rectifying column has a temperature of 185° C and has the following composition:
 895 tons of $NH_3$
 552 tons of $CO_2$
 498 tons of $H_2O$
 1,085 tons of urea.

The solution passed on from rectifying column 5 to one-pass heater 8 via line 6 contains:
 885 tons of $NH_3$ 539 tons of $CO_2$
532 tons of $H_2O$
1,085 tons of urea.

The temperature of the solution is to 190° C additional heat being added by return gases via line 20, which in heater 8 is increased to 210° C by combustion of 55,440 m³ of natural gas. The heat-exchange surface area required for this purpose is 367 m². The mixture of gas and liquid formed by heating in heater 8 is introduced into the top part of column 16 which is provided with vertical plates along which the liquid flows downward counter-currently with 734 tons of $CO_2$ required for the synthesis, which $CO_2$ has a temperature of 120° C and has been fed into the bottom part of the column. The column is operated under adiabatic conditions. From column 16 a solution is discharged which contains, in addition to 1,000 tons of urea and 427 tons of $H_2O$, 100 tons of $NH_3$ and 118 tons of $CO_2$ and has a temperature of 160° C.

The gaseous mixture separated off in stripping column 16 and led into the bottom part of rectifying column 5 contains:

833 tons of $NH_3$
1,216 tons of $CO_2$
80 tons of $H_2O$.

From the top of rectifying column 5 a gas mixture is discharged to condenser 22, which mixture is composed of 843 tons of $NH_3$
1,230 tons of $CO_2$
46 tons of $H_2O$.

The dilute ammonium carbamate solution led from the low-pressure stage beyond reducer 19 to gas scrubber 25 forms a solution together with the components therein absorbed out of the purge gas mixture, which solution contains:

199 tons of $NH_3$
203 tons of $CO_2$
131 tons of $H_2O$, and is also led into condenser 22. In the condenser 1,025 tons of 4 atm steam are formed.

For the sake of comparison, it is noted that using the known process described in the background of the invention portion above, in which the heat required is supplied during the treatment with the stripping gas, a heat-exchange surface area of approximately 800 m² would be necessary to achieve substantially similar results as regards urea production.

What we claim is:

1. In a process for synthesizing urea by reacting carbon dioxide and ammonia at a pressure of 80–200 atm. and a temperature of 170°–190° C. in a urea synthesis zone, heating the thus-produced urea synthesis solution and contacting said solution with a stripping gas, thereby forming a gaseous mixture composed primarily of ammonia, carbon dioxide and water vapor, and recirculating said gaseous mixture, said heating and contacting being effected at substantially the same pressure as that maintained in the urea synthesis zone, the improvement comprising:

a. in a first step, increasing the temperature of said urea synthesis solution by said heating to a temperature of 205°–250° C. in a heat exchange zone thereby liberating a mixture of gases prior to contact with said stripping gas, and b. in a second step, effecting said contacting of the heated synthesis solution of the first step (a) with said stripping gas under substantially adiabatic conditions, thereby removing and expelling the unconverted reactants with said stripping gas.

2. The process as claimed in claim 1 wherein said urea synthesis solution is passed co-currently through the heat exchange zone with the gas mixture liberated by said heating step (a).

3. The process as claimed in claim 1 wherein heating step (a) is conducted in a one-pass heater.

4. The process as claimed in claim 1 wherein the heating step (a) is conducted by combustion of a gaseous or liquid hydrocarbon fuel.

5. The process as claimed in claim 1 wherein the residence time of said urea synthesis solution in said heat exchange zone is at most about 10 seconds.

6. The process as claimed in claim 1 wherein water is removed from the gas mixture resulting from step (b) by countercurrently contacting said gas mixture with said urea synthesis solution just prior to heating step (a), thereby increasing the temperature of said solution.

* * * * *